(12) United States Patent
Papasso et al.

(10) Patent No.: US 6,239,092 B1
(45) Date of Patent: *May 29, 2001

(54) THICKENED ACIDIC, HARD SURFACE CLEANING AND DISINFECTING COMPOSITIONS PARTICULARLY USEFUL FOR CERAMIC SURFACES

(75) Inventors: Thomas Michael Papasso, Staten Island, NY (US); Michael David Love, Parsippany, NJ (US); James William Cavanagh, Ramsey, NJ (US); Robert Terrence Fellows, Park Ridge, NJ (US)

(73) Assignee: Reckitt Benckiser Inc., Wayne, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/144,701

(22) Filed: Sep. 1, 1998

(30) Foreign Application Priority Data

Sep. 30, 1997 (GB) .................................................. 9720690

(51) Int. Cl.[7] ....................................................... C11D 3/16
(52) U.S. Cl. .......................... 510/238; 510/319; 510/384; 510/423; 510/473; 510/488
(58) Field of Search .................................. 510/384, 319, 510/423, 473, 488, 238

(56) References Cited

U.S. PATENT DOCUMENTS

| | | | | |
|---|---|---|---|---|
| 4,164,477 | * | 8/1979 | Whitley ................................. | 252/99 |
| 4,246,130 | | 1/1981 | Koch ..................................... | 252/143 |
| 4,287,082 | * | 9/1981 | Tolfo et al. ...................... | 252/174.12 |
| 4,581,042 | * | 4/1986 | Willmore ............................... | 51/293 |
| 4,842,771 | * | 6/1989 | Rorig et al. ........................... | 252/547 |
| 5,000,867 | * | 3/1991 | Heinhuis-Walther et al. ...... | 252/106 |
| 5,320,783 | * | 6/1994 | Marin et al. ......................... | 252/544 |
| 5,733,859 | * | 3/1998 | Carrie et al. .......................... | 510/362 |

FOREIGN PATENT DOCUMENTS

| | | | | |
|---|---|---|---|---|
| 0 265 202 | | 4/1988 | (EP) | A01N/59/26 |
| 0 606 712 A1 | | 7/1994 | (EP) | C11D/3/20 |
| 0 621 335 A2 | | 10/1994 | (EP) | C11D/1/835 |
| 0 651 048 A2 | | 5/1995 | (EP) | C11D/1/835 |
| 0 651 049 A2 | | 5/1995 | (EP) | C11D/1/835 |
| 2 194 957 | | 3/1988 | (GB) | C11D/3/48 |
| 2 306 500 | | 7/1997 | (GB) | C11D/3/43 |
| WO94/13769 | | 6/1994 | (WO) | C11D/1/62 |

\* cited by examiner

*Primary Examiner*—William Krynski
*Assistant Examiner*—Dawn L. Garrett
(74) *Attorney, Agent, or Firm*—Fish & Richardson P.C.

(57) ABSTRACT

Acidic, thickened cleaning and disinfecting compositions which exhibit good long term shelf stability, are particularly effective in the removal of limescale from hard surfaces, and which are effective against gram positive and gram negative bacteria. The compositions comprise one or more nonionic surfactants; one or more quaternary ammonium surfactant compounds having germicidal properties; an acid mixture comprising formic acid and one or more water soluble organic acids, particularly water soluble organic acids selected from the group consisting of: lactic acid, citric acid, glycolic acid and where the formic acid and one or more water soluble organic acids are present in a weight ratio of formic acid: formic acid:water soluble organic acid(s) of 1:0.1–10; a cellulose based thickening composition; optionally but desirably a one or more conventional additives such as a coloring agent, fragrance or pH adjusting agent; and, water. The compositions may also include further conventional adjuvants such as perfumes and coloring agents in minor amounts. The compositions feature surprisingly good viscosity retention over time notwithstanding the presence of formic acid and cellulose based thickeners in the compositions.

25 Claims, No Drawings

THICKENED ACIDIC, HARD SURFACE CLEANING AND DISINFECTING COMPOSITIONS PARTICULARLY USEFUL FOR CERAMIC SURFACES

The present invention relates to thickened cleaning and disinfecting compositions which are acidic in nature, and which exhibit good cleaning, disinfecting and long term stability.

While the prior art has provided various compositions directed to cleaning and disinfecting hard surfaces, particularly lavatory surfaces there is yet a continuing need in the art for thickened aqueous compositions which provide: satisfactory cleaning especially of limescale deposits from metal, enamel and porcelain surfaces as found on lavatory fixtures, disinfection of hard surfaces and good long term stability of the thickened compositions.

The present invention provides stable thickened aqueous acidic hard surface cleaning and disinfecting composition which comprises:

one or more nonionic surfactants, particularly linear primary alcohol ethoxylates;

one or more quaternary ammonium surfactant compounds having germicidal properties;

an acid mixture comprising formic acid and one or more water soluble organic acids, particularly water soluble organic acids selected from the group consisting of: lactic acid, glycolic acid and citric acid and particularly where the acid mixture include formic acid and at least one other water soluble organic acid wherein these acids are present in a weight ratio of formic acid:water soluble organic acids of 1:0.1–10;

a cellulose based thickening composition;

optionally but desirably a pH adjusting agent, fragrance, coloring agent;

and, water.

The aqueous acidic hard surface cleaning and disinfecting composition may further include minor amounts, i.e., less than a combined total amount of 10%wt., of conventional additives including but not limited to: colorants such as pigments and dyes; fragrances and perfumes, pH adjusting agents as well as other conventional additives. Most desirably, these compositions are effective against both gram positive and gram negative bacteria.

The present invention also provides a method for cleaning (especially the removal of limescale deposits) and disinfecting from metal, enamel and porcelain surfaces as found on lavatory fixtures.

The compositions include one or more nonionic surfactants. These are well known, and any of these are expected to be useful in the inventive compositions. Exemplary useful nonionic surfactants include condensation products of alkylene oxide groups with an organic hydrophobic compound, such as an aliphatic or alkyl aromatic compound. Further exemplary useful nonionic surfactants include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides. Also contemplated as useful are ethoxylated alkyl phenols such as octylphenolethoxylates and nonylphenolethoxylates.

Preferred nonionic surfactants are ethoxylated alcohols. The compounds are well known and may be formed by condensation of an alcohol, or mixtures thereof, with sufficient ethylene oxide to produce a compound having a polyoxyethylene. Preferably the number of ethylene oxide units are present in an amount sufficient to insure solubility of the compound in an aqueous composition of this invention or in any dilution thereof. Desirably, the ethoxylated alcohols are produced by condensation of about 4–20, more preferably 6–18 moles of ethylene oxide with 1 mole of the linear primary aliphatic alcohol. The aliphatic alcohol may be linear or may be branched, and may be a primary, secondary or tertiary alcohol (including by way of non-limiting example: decyl alcohol, dodecyl alcohol, tridecyl alcohol, hexadecyl alcohol, octadecyl alcohol, and the like). As known to those skilled in the art, the number of moles of ethylene oxide which are condensed with one mole of aliphatic alcohol depends upon the molecular weight of the hydrophobic portion of the condensation product. The aliphatic alcohols are desirably a primary, secondary or tertiary aliphatic alcohol having about 10–20, and preferably 11–17, carbon atoms, and most preferably is an alcohol having 12–16 carbon atoms Especially preferably the nonionic surfactant of the present inventive compositions is the condensation product of linear or branched $C_{12}$–$C_{16}$ aliphatic alcohols, especially $C_{12}$–$C_{16}$ linear aliphatic alcohols or mixtures thereof, with sufficient ethylene oxide to provide an average of from 6–12 moles of ethylene oxide per molecule. Most preferably the nonionic surfactant constituent consists solely of linear or branched $C_{12}$–$C_{16}$ aliphatic alcohols with 6–9 moles of ethylene oxide per molecule.

The nonionic surfactant is present in any effective amount, but generally is present in an amount of up to about 10% by weight, based on the total weight of the composition. Desirably the nonionic surfactant is present in an amount of from about 0.01%wt. to about 8%wt, and most desirably is present in an amount of from about 0.1%wt. to about 5%wt.

The compositions according to the invention include one or more quaternary ammonium surfactant compounds having germicidal properties; these compounds provide a sanitizing effect. Particularly useful quaternary ammonium compounds and salts thereof include quaternary ammonium germicides which may be characterized by the general structural formula:

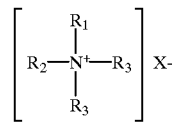

where at least one of $R_1$, $R_2$, $R_3$ and $R_4$ is a hydrophobic, aliphatic, aryl aliphatic or aliphatic aryl radical of from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming anionic radical.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are found useful in the practice of the present invention include those which have the structural formula:

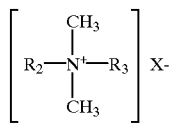

wherein $R_2$ and $R_3$ are the same or different $C_1$–$C_{12}$ alkyl, or $R_2$ is $C_{12-16}$ alkyl, $C_{8-18}$ alkylethoxy, $C_{8-18}$ alkylphenolethoxy and $R_3$ is benzyl, and X is a halide, for example chloride, bromide or iodide, or is a methosulfate counterion. The alkyl groups recited in $R_2$ and $R_3$ may be straight chained or branched, but are preferably substantially linear.

Particularly useful quaternary germicides include compositions which include a single quaternary, as well as mixtures of two or more different quaternary. Particularly useful quaternary germicides include BARDAC® 205M, and BARDAC® 208M or BTC® 885 which is described to be a blend of alkyl dimethyl benzyl ammonium chlorides; BARDAC® 2050 and BARDAC® 2080 or BTC® 818 which is described to be based on dialkyl($C_8$–$C_{10}$)dimethyl ammonium chloride; BARDAC® 2250 and BARDAC® 2280 or BTC® 1010 which is described to be a composition which includes didecyl dimethyl ammonium chloride; BARDAC® LF and BARDAC® LF 80 which is described to be based on dioctyl dimethyl ammonium chloride; BARQUAT® MB-50, HYAMINE® 3500, BARQUAT® MB-80, BTC® 835, BTC® 8358 or BTC® 65 USP each described to be based on alkyl dimethyl benzyl ammonium chloride; BARQUAT® MX-50, BARQUAT® MX-80, BTC® 824 or BTC® 8248 each described to be a composition based on alkyl dimethyl benzyl ammonium chloride; BARQUAT® OJ-50, BARQUAT® OJ-80, BTC® 2565, or BTC®& 2658 each described to be a composition based on alkyl dimethyl benzyl ammonium chloride; BARQUAT® 4250, BARQUAT® 4280, BARQUAT® 4250Z, BARQUAT® 4280Z, BTC® 2125, or BTC® 2125M each described to be a composition based on alkyl dimethyl benzyl ammonium chloride and/or alkyl dimethyl ethyl benzyl ammonium chloride; BARQUAT® MS-100 or BTC® 324-P-100 each described to be based on myristyl dimethyl benzyl ammonium chloride; HYAMINE® 2389 described to be based on methyl dodecyl benzyl ammonium chloride and/or methyl dodecyl xylene-bis-trimethyl ammonium chloride; HYAMINE® 1622 described to be an aqueous solution of benzethonium chloride; HYAMINE® 3500-NF or BTC® 50 each described to be based on alkyl dimethyl benzyl ammonium chloride; as well as BARQUAT® 1552 or BTC® 776 described to be based on alkyl dimethyl benzyl ammonium chloride and/or dialkyl methyl benzyl ammonium chloride. (Each of these recited materials are presently commercially available from Lonza, Inc., Fairlawn, N.J. and/or from Stepan Co., Northfield Ill.).

These quaternary ammonium surfactant compounds may be present in any effective amount, but and are effective in amounts from as little as 0.001%wt. Typically, these compounds are present in amounts of from 0.01–10% by weight, based on the total weight of the composition. Desirably these compounds are present in amounts from 0.01–7%wt, more desirably from 0.1–5%wt., and most desirably from 0.1–3%wt.

These quaternary ammonium compounds are usually provided in an alcohol such as a $C_1$–$C_6$ alcohol (i.e., ethanol, n-propanol, isopropanol, n-butanol, sec-butanol) or in an aqueous/alcohol mixture containing such alcohols. While these alcohols are present in only a very minor amount as they are supplied as part of the quaternary ammonium compounds it is believed they contribute to the antimicrobial efficacy of the invention. Therefore, it is preferred that up to about 1%wt. of a $C_1$–$C_6$ alcohol, preferably 0.001–1%wt., more preferably 0.01–0.75%wt. be present in the inventive compositions.

In the cleaning compositions according to the invention, the quaternary ammonium compound constituent is required to be present in amounts which are effective in exhibiting satisfactory germicidal activity against selected bacteria sought to be treated by the cleaning compositions. Such efficacy may be achieved against less resistant bacterial strains with only minor amounts of the quaternary ammonium compounds being present, while more resistant strains of bacteria require greater amounts of the quaternary ammonium compounds in order to destroy these more resistant strains. The quaternary ammonium compound need only pre present in germicidally effective amounts, but may be present in amounts from 0.01%–10% wt. based on the total weight of the composition of which they form a part. Generally, effective "hospital strength" germicidal efficacy meeting current EPA guidelines is provided when the quaternary ammonium compounds are present in an amount of from about 0.05%wt. to about 5%wt. Desirably in the compositions of the instant invention, the quaternary ammonium compounds is present in an amount of from 0.05%wt. to about 3%wt, based on the total weight of the inventive compositions being taught herein.

An essential feature of the inventive compositions is an acid mixture comprising formic acid and one or more water soluble organic acids, particularly water soluble organic acids. The acid mixture may be present in any effective amount, but desirably is not present in amounts of more than about 10%wt. based on the total weight of the compositions. Desirably the acid mixtures form from 0.01–10%wt., more desirably from 0.1–10%wt. of the compositions. The water soluble organic acids include at least two carbon atoms, and include at least one carboxyl group (—COOH) in its structure. Particularly useful as water soluble organic acids are formic acid and an acid selected from the group consisting of: lactic acid, citric acid, and glycolic acid. The formic acid and the further water soluble organic acid in the acid mixture are present in a weight ratio of formic acid:water soluble organic acids of 1:0.1–10, and desirably 1:0.25–2.5, and more desirably from 1:0.5–1.75. Particularly advantageous ratios are indicated in the Examples. While various organic acids such as and including these acids may have been used in the past, usually singly, the present inventors have surprisingly discovered an apparent synergistic effect from the acid mixtures described. It has been surprisingly discovered that the long term stability of the cellulose containing compositions is achieved when the formic acid is present with one or more water soluble organic acids (or water soluble salt forms thereof), particularly in the weight ratios described. In the prior art, cellulose thickeners have not been typically used in the presence of formic acid, which acid is very desirable as it is particularly effective in removing limescale. According to the present invention, the use of one or more water soluble organic acids in conjunction with formic acid substantially reduces the loss of viscosity of the thickened compositions to a degree greater than would be expected. This is surprising as the presence of the acids in such compositions is expected to quickly degrade other constituents which may be present, especially thickeners such as described below. This is particularly true in compositions which contain formic acid in conjunction with cellulose based materials as formic acid is known to quickly degrade such cellulose based materials.

This surprising benefit is frequently very apparent when formic acid is present in conjunction with two (or more) different water soluble organic acids. This has been to be particularly true where the ratio of the formic acid: (total weight of the two or more different water soluble organic acids) is a ratio of: 1:(0.1–10). Where three different water soluble organic acids are present, desirably these are present in a weight ratio of formic acid:first water soluble organic acid:second water soluble organic acid of 1:0.1–10:0.1–10, especially when these are present in a weight ratios of: 1:0.25–2.5:0.25–2.5, and most especially in a weight ratio of 1:0.5–1.75:0.5–1.75. Particularly advantageous ratios are indicated in the Examples.

The presence of formic acid in conjunction with at least one further water soluble organic acids in the weight ratios described above provide good cleaning, and have been found to suffer a reduced loss of viscosity under the conditions of accelerated aging testing at elevated temperatures, particularly under the test protocol described in the examples. This is particularly important as the compositions are acidic in nature.

The inventive compositions desirably feature low odor, are virtually transparent (in the absence of coloring agents) ever after high temperature stability testing, and are easy to disperse onto surfaces to be cleaned and disinfected.

As noted, the compositions of the invention are thickened and have a viscosity greater than water. The actual degree of thickening is dependent on the amount of thickener included in a composition. Thickeners which may be used are cellulose based thickeners including but not limited to: methyl cellulose, methylethyl cellulose, hydroxymethyl cellulose, hydroxyethyl cellulose, carboxymethyl cellulose, and the like. Generally the thickener is present in not more than about 10%wt. based on the total weight of the composition of which it forms a part. Desirably the thickener is present in an amount of from 0.01–5%wt., and more desirably from 0.01–2%wt. Starch based thickeners, including so called modified starch based thickeners as frequently encountered in the foods industry are also contemplated as being useful.

The compositions of the invention are acidic, and exhibit a pH of less than 7, more preferably about 4.5 and less and most preferably from 3–4.5. Whereas the presence of the acid mixture described above will impart acidity to the composition, it is frequently desirable to include a buffer or pH adjusting agent to the compositions to maintain the compositions approximately at a desired pH (or pH range). Exemplary useful pH buffers include inorganic and organic buffering agent, and especially include alkali metal and alkaline earth metal hydroxides such as sodium hydroxide and potassium hydroxide. Others not described here may also be used. Particularly preferred is sodium hydroxide which is widely available at low cost, and is effective.

Such materials as described above are each individually known to the art, many of which are described in *McCutcheon's Emulsifiers and Detergents* (Vol. 1), *McCutcheon's Functional Materials* (Vol. 2), North American Edition, 1991; *Kirk-Othmer, Encyclopedia of Chemical Technology*, 3rd Ed., Vol. 22, the contents of which are herein incorporated by reference For any particular composition described above, any optional ingredients should be compatible with the other ingredients present.

As is noted above, the compositions according to the invention are aqueous in nature. Water is added to order to provide to 100% by weight of the compositions of the invention. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the aqueous compositions according to the invention.

The compositions may be made by simply mixing measured amounts of the individual constituents into water, at room temperature under constant stirring until a homogenous mixture is attained. In a preferred method, a first premixture is made by mixing together the nonionic and fragrance constituents. A second premixture is made by mixing the water, cellulose thickener and optionally, sodium hydroxide to form a homogeous mixture. Thereafter, the first premixture is added to the second premixture, after which the remaining constituents are added, and mixing continues until a homogenous mixture is attained.

According to certain preferred embodiments of the invention there are provided thickened aqueous acidic hard surface cleaning and disinfecting compositions which consist essentially of:

0.1–10%wt. one or more nonionic surfactants;

0.1–10%wt. of one or more quaternary ammonium surfactant compounds having germicidal properties;

0.001–1% of a $C_1$–$C_6$ alcohol;

0.1–10%wt. an acid mixture comprising formic acid and one or more water soluble organic acids, particularly water soluble organic acids selected from the group consisting of: lactic acid, glycolic acid and citric acid and particularly where the acid mixture include formic acid and at least one other water soluble organic acid wherein these acids are present in a weight ratio of formic acid:water soluble organic acids of 1:0.1–10;

0.01–5%wt. a cellulose based thickening composition;

optionally up to 10%wt. of one or more optional constituents, with the remaining balance to 100%wt. of water.

The thickened aqueous acidic hard surface cleaning and disinfecting composition according to the invention is desirably provided as a ready to use product which may be directly applied to a hard surface. By way of example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted include those associated with kitchen environments and other environments associated with food preparation. The inventive compositions are particularly useful in cleaning and disinfecting lavatory fixtures such as shower stalls, bathtubs and bathing appliances (racks, curtains, shower doors, shower bars) toilets, bidets, wall and flooring surfaces especially those which include refractory materials and the like. The inventive compositions especially particularly useful in the cleaning and disinfecting of lavatory fixtures, especially toilets and bidets. They may be packaged in any suitable container particularly flasks or bottles, including squeeze-type bottles, as well as bottles provided with a spray apparatus which is used to dispense the composition by spraying.

In a yet further aspect of the invention there is provided an thickened aqueous composition which includes a cellulose based thickener, an acid mixture comprising formic acid and one or more water soluble organic acids, particularly water soluble organic acids selected from the group consisting of: lactic acid, glycolic acid and citric acid and particularly where the acid mixture include formic acid and at least one other water soluble organic acid wherein these acids are present in a weight ratio of formic acid:water soluble organic acids of 1:0.1–10; and optionally one or more detersive sufactants.

The compositions according to the invention, including certain preferred embodiments of the invention are presented in the following examples.

EXAMPLES

A number of formulations according to the invention (indicated as Examples, "E") as well as several comparative examples (indicated as Comparatives, "C") were produced. Each of these were made were mixing the constituents outlined on Table 1 by adding the individual constituents into a beaker of deionized water at room temperature (68° F., 20° C.) which was stirred with a conventional magnetic stirring rod. Stirring continued until the formulation was homogenous in appearance. It is to be noted that the constituents might be added in any order, but it is preferred that water be the initial constituent provided to a mixing vessel or apparatus as it is the major constituent and addition of the further constituents thereto is convenient. Also, it is convenient to disperse the cellulose thickener into a premixture with a quantity of water, and to add this premixture to the beaker. The exact compositions of the example formulations are listed on Table 1, below.
Evaluation of Shelf Stability:

Formulations according to the invention and described on Table 1 were evaluated in order to determine their initial viscosity. The weights indicated on Table 1 indicate the amount of the named constituent, and are to be understood to represent 100%wt. actives of each named constituent. The source of the named constituents are described in more detail in the following Table. Each of the constituents on Table 1.

| Table (Constituents) | |
|---|---|
| linear alcohol ethoxylate | supplied by GENAPOL 26-L-60, a linear $C_{12}$–$C_{16}$ alcohol ethoxylate, with an average of 7.3 ethylene oxide groups per molecule (100% wt. actives) |
| quaternary ammonium chlorides | supplied by BTC-888 (Stepan Chem. Co.) a blend of dialkyl dimethyl benzyl ammonium chloride, and alkyl dimethyl benzyl ammonium chloride (80% wt. actives) which includes 10% wt. ethanol |
| hydroxyethyl cellulose | supplied by CELLOSIZE QP-100MH from Union Carbide Co. (Danbury, CT) (100% wt. actives) |
| formic acid | aqueous, technical grade, Aldrich Co. or other supplier (94% wt. actives) |
| citric acid | aqueous, technical grade, Aldrich Co. or other supplier (100% wt. actives) |
| glycolic acid | aqueous, technical grade, Aldrich Co. or other supplier (57% wt. actives) |
| fragrance and dye | proprietary compositions of their respective manufacturers |
| di water | deionized water |

All viscosity measurements were performed on aliquots of a formulation at room temperature with a Brookfield Viscometer, fitted with a LV-2 spindle at a rotational speed of 60 rpm at 22° C. Viscosity measurement results are reported in centipoise at on Tables 2A, 3A below. Formulations were placed in sealed glass containers, and subjected to an accelerated aging test wherein the formulations were maintained at 120° F. (48.5° C.) for a period of 6 weeks. At weekly intervals, aliquots of each formulation were taken and used to determine the viscosity in the manner outlined above. Similarly, the results are reported on Tables 2A, 3A below. The cumulative total loss of viscosity, at weekly intervals is reported on Tables 2B and 3B below.

TABLE 1

| Formulation: | linear alcohol ethoxylate | quaternary ammonium chlorides | hydroxy ethyl cellulose | fragrance and dye | formic acid | citric acid | glycolic acid | deionized water | Ratio: Formic acid: α-hydroxy organic acid | Ratio: Formic acid: 1st α-hydroxy organic acid: 2nd α-hydroxy organic acid | Initial pH |
|---|---|---|---|---|---|---|---|---|---|---|---|
| C1 | 0.5 | 1.1 | 0.5 | 0.35 | 2.35 | 0 | 0 | to 100 | 1:0 | 1:0:0 | 3.50 |
| C2 | 0.5 | 1.1 | 0.5 | 0.35 | 0 | 2.5 | 0 | to 100 | — | — | 3.52 |
| C3 | 0.5 | 1.1 | 0.5 | 0.35 | 0 | 0 | 1.43 | to 100 | — | — | 3.52 |
| C4 | 0.5 | 1.1 | 0.5 | 0.35 | 0 | 1.25 | 0.71 | to 100 | — | — | 3.55 |
| E1 | 0.5 | 1.1 | 0.5 | 0.35 | 1.175 | 0 | 0.71 | to 100 | 1:0.6 | 1:0:0.6 | 3.50 |
| E2 | 0.5 | 1.1 | 0.5 | 0.35 | 1.175 | 1.25 | 0 | to 100 | 1:1.06 | 1:1.06:0 | 3.51 |
| E3 | 0.5 | 1.1 | 0.5 | 0.35 | 0.78 | 0.83 | 0.47 | to 100 | 1:1.66 | 1:1.06:0.6 | 3.52 |
| E4 | 0.5 | 1.1 | 0.5 | 0.35 | 0.78 | 0.83 | 0.47 | to 100 | 1:1.66 | 1:1.06:0.6 | 3.51 |
| C5 | 0.5 | 1.1 | 0.5 | 0.35 | 2.35 | 0 | 0 | to 100 | 1:0 | 1:0:0 | 4.04 |
| C6 | 0.5 | 1.1 | 0.5 | 0.35 | 0 | 2.5 | 0 | to 100 | — | — | 4.05 |
| C7 | 0.5 | 1.1 | 0.5 | 0.35 | 0 | 0 | 1.43 | to 100 | — | — | 4.04 |

TABLE 1-continued

| Formulation: | linear alcohol ethoxylate | quaternary ammonium chlorides | hydroxy ethyl cellulose | fragrance and dye | formic acid | citric acid | glycolic acid | deionized water | Ratio: Formic acid: α-hydroxy organic acid | Ratio: Formic acid: 1st α-hydroxy organic acid: 2nd α-hydroxy organic acid | Initial pH |
|---|---|---|---|---|---|---|---|---|---|---|---|
| C8 | 0.5 | 1.1 | 0.5 | 0.35 | 0 | 1.25 | 0.71 | to 100 | — | — | 4.03 |
| E5 | 0.5 | 1.1 | 0.5 | 0.35 | 1.175 | 1.25 | 0 | to 100 | 1:1.06 | 1:1.06:0 | 4.00 |
| E6 | 0.5 | 1.1 | 0.5 | 0.35 | 1.175 | 0 | 0.71 | to 100 | 1:0.6 | 1:0:0.6 | 4.01 |
| E7 | 0.5 | 1.1 | 0.5 | 0.35 | 0.78 | 0.83 | 0.47 | to 100 | 1:1.66 | 1:1.06:0.6 | 4.04 |
| E8 | 0.5 | 1.1 | 0.5 | 0.35 | 0.78 | 0.83 | 0.47 | to 100 | 1:1.66 | 1:1.06:0.6 | 4.03 |

TABLE 2A (pH = 3.5)

| Formulation: | Initial pH | Initial Viscosity | Week 1 (cps) | Week 2 (cps) | Week 3 (cps) | Week 4 (cps) | Week 5 (cps) | Week 6 (cps) |
|---|---|---|---|---|---|---|---|---|
| C1 | 3.50 | 407.0 | 331.0 | 294.0 | 272.0 | 245.0 | 224.0 | 197.0 |
| C2 | 3.52 | 417.0 | 334.0 | 282.0 | 264.0 | 210.0 | 175.0 | 150.0 |
| C3 | 3.52 | 438.0 | 364.0 | 342.o | 334.0 | 302.0 | 272.0 | 267.0 |
| C4 | 3.55 | 426.0 | 339.0 | 322.0 | 301.0 | 267.0 | 257.0 | 202.0 |
| E1 | 3.50 | 396.0 | 324.0 | 309.0 | 286.0 | 262.0 | 261.0 | 214.0 |
| E2 | 3.51 | 416.0 | 369.0 | 309.0 | 296.0 | 259.0 | 222.0 | 205.0 |
| E3 | 3.52 | 406.0 | 337.0 | 311.0 | 289.0 | 261.0 | 250.0 | 195.0 |
| E4 | 3.51 | 417.0 | 346.0 | 322.0 | 306.0 | 265.0 | 234.0 | 209.0 |

TABLE 2B (pH = 3.5)

| Formulation: | Initial pH | Initial Viscosity | Cumulative % Viscosity loss @ week 1 | Cumulative % Viscosity loss @ week 2 | Cumulative % Viscosity loss @ week 3 | Cumulative % Viscosity loss @ week 4 | Cumulative % Viscosity loss @ week 5 | Cumulative % Viscosity loss @ week 6 |
|---|---|---|---|---|---|---|---|---|
| C1 | 3.50 | 407.0 | 18.67% | 27.76% | 33.17% | 39.80% | 40.05% | 51.60% |
| C2 | 3.52 | 417.0 | 19.90% | 32.37% | 36.69% | 49.64% | 58.03% | 64.03% |
| C3 | 3.52 | 438.0 | 16.89% | 21.92% | 23.74% | 31.05% | 37.90% | 39.04% |
| C4 | 3.55 | 426.0 | 20.42% | 24.41% | 29.34% | 37.32% | 39.67% | 52.58% |
| E1 | 3.50 | 396.0 | 18.18% | 21.97% | 27.78% | 33.84% | 34.09% | 45.96% |
| E2 | 3.51 | 416.0 | 11.30% | 25.72% | 28.85% | 37.74% | 46.63% | 50.72% |
| E3 | 3.52 | 406.0 | 17.00% | 23.40% | 28.82% | 35.71% | 38.42% | 51.97% |
| E4 | 3.51 | 417.0 | 17.03% | 22.78% | 26.62% | 36.45% | 43.88% | 43.88% |

TABLE 3A (pH = 4)

| Formulation: | Initial pH | Initial Viscosity | Week 1 (cps) | Week 2 (cps) | Week 3 (cps) | Week 4 (cps) | Week 5 (cps) | Week 6 (cps) |
|---|---|---|---|---|---|---|---|---|
| C5 | 4.04 | 424.0 | 329.0 | 269.0 | 254.0 | 209.0 | 174.0 | 158.0 |
| C6 | 4.05 | 417.0 | 362.0 | 341.0 | 316.0 | 292.0 | 272.0 | 240.0 |
| C7 | 4.04 | 446.0 | 384.0 | 384.0 | 384.0 | 356.0 | 336.0 | 336.0 |
| C8 | 4.03 | 429.0 | 386.0 | 379.0 | 354.0 | 342.0 | 344.0 | 294.0 |
| E5 | 4.00 | 409.0 | 381.0 | 351.0 | 356.0 | 322.0 | 299.0 | 297.0 |
| E6 | 4.01 | 441.0 | 397.0 | 387.0 | 394.0 | 359.0 | 339.0 | 344.0 |
| E7 | 4.04 | 438.0 | 397.0 | 392.0 | 379.0 | 362.0 | 354.0 | 321.0 |
| E8 | 4.03 | 424.0 | 379.0 | 379.0 | 359.0 | 336.0 | 336.0 | 299.0 |

TABLE 3B

| | | | Cumulative % Viscosity loss @ week 1 | Cumulative % Viscosity loss @ week 2 | Cumulative % Viscosity loss @ week 3 | Cumulative % Viscosity loss @ week 4 | Cumulative % Viscosity loss @ week 5 | Cumulative % Viscosity loss @ week 6 |
|---|---|---|---|---|---|---|---|---|
| Formulation: | Initial pH | Initial Viscosity | | | (pH = 4) | | | |
| C5 | 4.04 | 424.0 | 22.41% | 36.56% | 40.09% | 50.71% | 58.96% | 62.74% |
| C6 | 4.05 | 417.0 | 13.19% | 18.23% | 24.22% | 29.98% | 34.77% | 42.45% |
| C7 | 4.04 | 446.0 | 13.90% | 13.90% | 13.90% | 20.18% | 24.66% | 24.66% |
| C8 | 4.03 | 429.0 | 10.02% | 11.66% | 17.48% | 20.28% | 19.81% | 31.47% |
| E5 | 4.00 | 409.0 | 6.85% | 14.18% | 12.96% | 21.27% | 26.89% | 27.38% |
| E6 | 4.01 | 441.0 | 9.98% | 12.24% | 10.66% | 18.59% | 23.13% | 22.00% |
| E7 | 4.04 | 438.0 | 9.36% | 10.50% | 13.47% | 17.35% | 19.18% | 26.71% |
| E8 | 4.03 | 424.0 | 10.61% | 10.61% | 15.33% | 20.75% | 20.75% | 29.48% |

Subsequent to this accelerated aging test, all of the formulations were observed to each be a colored, substantially transparent single phase mixture with good flow properties; bulk phase separation was not observed to occur.

Evaluation of Antimicrobial Efficacy:

A formulation according to the invention was prepared from the following constituents:

| | Example A |
|---|---|
| 0.50% | hydroxyethyl cellulose |
| 0.50% | linear $C_{12}$–$C_{16}$ alcohol ethoxylate, with an average of 7.3ethylene oxide groups per molecule |
| 1.50% | quaternary ammonium chloride |
| 1.10% | formic acid |
| 1.40% | glycolic acid |
| ~1.0% | sodium hydroxide |
| ~0.4% | fragrance and dyes |
| to 100% | deionized water |

The weight percentages for Example A indicate the actual weight of the indicated materials, which were supplied from the constituents were the same as used to form the formulations indicated on Table 1, above. This formulation was evaluated in order to evaluate its antimicrobial efficacy against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). The testing was performed in accordance with the protocols outlined in "Use-Dilution Method", Protocols 955.14, 955.15 and 964.02 described in Chapter 6 of "Official Methods of Analysis", 16$^{th}$ Edition, of the Association of Official Analytical Chemists; "Germicidal and Detergent Sanitizing Action of Disinfectants", 960.09 described in Chapter 6 of "Official Methods of Analysis", 15$^{th}$ Edition, of the Association of Official Analytical Chemists; or American Society for Testing and Materials (ASTM) E 1054-91 the contents of which are herein incorporated by reference. This test is also commonly referred to as the "AOAC Use-Dilution Test Method".

As is appreciated by the skilled practitioner in the art, the results of the AOAC Use-Dilution Test Method indicates the number of test substrates wherein the tested organism remains viable after contact for 10 minutes with a test disinfecting composition/total number of tested substrates (cylinders) evaluated in accordance with the AOAC Use-Dilution Test. Thus, a result of "0/60" indicates that of 60 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition.

Results of the antimicrobial testing of the Example A formulation are indicated on Table 4, below. The reported results indicate the number of test cylinders with live test organisms/number of test cylinders tested for each example formulation and organism tested.

TABLE 4

| Antimicrobial Testing | | |
|---|---|---|
| *Staphylococcus aureus* | *Salmonella choleraesuis* | *Pseudomonas aeruginosa* |
| 0/60 | 0/60 | 0/60 |

As may be seen from the results indicated above, the compositions according to the invention provide excellent disinfection of hard surfaces.

While the invention is susceptible of various modifications, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

What is claimed is:

1. Thickened acidic hard surface cleaning and disinfecting composition comprising:
   one or more nonionic surfactants;
   one or more quaternary ammonium surfactant compounds having germicidal properties;
   an acid mixture comprising formic acid and one or more water soluble organic acids wherein these acids are present in a weight ratio of formic acid:water soluble organic acids of 1:0.1–10;
   a cellulose based thickening composition;
   optionally to 10%wt. of one or more optional constituents;
   and, water.

2. The composition according to claim 1 wherein the water soluble organic acids are selected from the group consisting of: lactic acid, glycolic acid and citric acid.

3. The composition according to claim 1 wherein the acid mixture comprises citric acid.

4. The composition according to claim 1 wherein the acid mixture comprises glycolic acid.

5. The composition according to claim 1 wherein the nonionic surfactant is a linear alcohol ethoxylate.

6. The composition according to claim 1 wherein the acid mixture contains at least formic acid, and at least two further different water soluble organic acids.

7. The composition according to claim 6 wherein the acid mixture contains formic acid, citric acid and glycolic acid.

8. The composition according to claim 1 wherein the formic acid and one or more water soluble organic acids are present in a weight ratio of formic acid:water soluble organic acids of 1:0.25–2.5.

9. The composition according to claim 1 which further comprises up to 1%wt. of a $C_1$–$C_6$ alcohol.

10. Thickened aqueous acidic hard surface cleaning and disinfecting composition according to claim 1 which consists essentially of:

0.1–10%wt. one or more nonionic surfactants;

0.001–10%wt. of one or more quaternary ammonium surfactant compounds having germicidal properties;

0.001–1% of a $C_1$–$C_6$ alcohol;

0.1–10%wt. of an acid mixture comprising formic acid and one or more water soluble organic acids where the formic acid and one or more water soluble organic acids are present in a weight ratio of formic acid:water soluble organic acids of 1:0.1–10;

0.01–5%wt. a cellulose based thickening composition;

optionally up to 10%wt. of one or more optional constituents, with the remaining balance to 100%wt. of water.

11. The composition according to claim 10 wherein the formic acid and one or more water soluble organic acids are present in a weight ratio of formic acid:water soluble organic acids of 1:0.25–2.5.

12. The composition according to claim 10 wherein the composition further includes colorants, fragrances, perfumes, or pH adjusting agents.

13. A thickened aqueous composition according to claim 1 which further includes one or more further detersive surfactants.

14. A process for cleaning limescale from a hard surface comprising the process step of:

contacting the hard surface having limescale thereon with a cleaning effective amount of the composition according to claim 1 to clean limescale present therefrom.

15. A process for cleaning limescale from a hard surface comprising the process step of:

contacting the hard surface having limescale thereon with a cleaning effective amount of the composition according to claim 10 to clean limescale present therefrom.

16. A thickened acidic hard surface cleaning and disinfecting composition which comprises:

0.1–10%wt. of one or more nonionic surfactants;

0.001–10%wt. of one or more quaternary ammonium surfactant compounds having germicidal properties;

0.1–10%wt. of an acid mixture consisting of formic acid and one or more water soluble organic acids wherein these acids are present in a weight ratio of formic acid:water soluble organic acids of 1:0.1–10;

0.01–5%wt. of a cellulose based thickening composition;

0–10%wt. of one or more optional constituents;

and, water.

17. The composition according to claim 16 wherein the water soluble organic acids are selected from the group consisting of: lactic acid, glycolic acid and citric acid.

18. The composition according to claim 16 wherein the acid mixture contains at least formic acid, and at least two further different water soluble organic acids.

19. The composition according to claim 16 wherein the acid mixture contains formic acid, citric acid and glycolic acid.

20. The composition according to claim 16 wherein the formic acid and one or more water soluble organic acids are present in a weight ratio of formic acid:water soluble organic acids of 1:0.25–2.5.

21. The composition according to claim 16 wherein the nonionic surfactant is a linear alcohol ethoxylate.

22. The composition according to claim 16 which further comprises up to 1%wt. of a $C_1$–$C_6$ alcohol.

23. The composition according to claim 16 which comprises one or more further detersive surfactants.

24. Thickened aqueous acidic hard surface cleaning and disinfecting composition according to claim 16 which consists essentially of:

0.1–10%wt. one or more nonionic surfactants;

0.001–10%wt. of one or more quaternary ammonium surfactant compounds having germicidal properties;

0.001–1% of a $C_1$–$C_6$ alcohol;

0.1–10%wt. of an acid mixture consisting of formic acid and one or more water soluble organic acids where the formic acid and one or more water soluble organic acids are present in a weight ratio of formic acid:water soluble organic acids of 1:0.1–10;

0.01–5%wt. a cellulose based thickening composition;

0–10%wt. of one or more optional constituents, with the remaining balance to 100%wt. of water.

25. The composition according to claim 24 wherein the formic acid and one or more water soluble organic acids are present in a weight ratio of formic acid:water soluble organic acids of 1:0.25–2.5.

* * * * *